United States Patent
Shelso et al.

[11] Patent Number: 6,149,680
[45] Date of Patent: Nov. 21, 2000

[54] STENT LOADING TOOL

[75] Inventors: Susan Irene Shelso, Plymouth; Mark Allan Blaskowski, Osseo; Doreen Mae Borgmann, Hopkins, all of Minn.

[73] Assignee: Scimed Life Systems, Inc., Maple Grove, Minn.

[21] Appl. No.: 09/326,757

[22] Filed: Jun. 4, 1999

Related U.S. Application Data

[60] Provisional application No. 60/087,919, Jun. 4, 1998.

[51] Int. Cl.[7] .............................. A61M 29/00; A61F 2/06
[52] U.S. Cl. ......................... 623/1.11; 604/160; 606/198
[58] Field of Search ................................. 606/108, 198; 623/1.11; 604/160, 161

[56] References Cited

U.S. PATENT DOCUMENTS

| | | | |
|---|---|---|---|
| 5,026,377 | 6/1991 | Burton et al. | 606/108 |
| 5,242,452 | 9/1993 | Inoue | 606/108 |
| 5,279,548 | 1/1994 | Essig et al. | 604/27 |
| 5,383,853 | 1/1995 | Jung et al. | 604/96 |
| 5,484,444 | 1/1996 | Braunschweiler et al. | 606/108 |
| 5,534,007 | 7/1996 | St. Germain et al. | 606/108 |
| 5,626,604 | 5/1997 | Cottone, Jr. | 606/198 |
| 5,628,754 | 5/1997 | Shevlin et al. | 606/108 |
| 5,630,830 | 5/1997 | Verbeek | 606/198 |
| 5,639,274 | 6/1997 | Fischell et al. | 604/96 |
| 5,672,169 | 9/1997 | Verbeek | 606/1 |
| 5,676,671 | 10/1997 | Inoue | 606/108 |
| 5,693,089 | 12/1997 | Ioue | 623/1 |
| 5,700,269 | 12/1997 | Pinchuk et al. | 606/108 |
| 5,725,519 | 3/1998 | Penner et al. | 606/1 |
| 5,738,674 | 4/1998 | Williams et al. | 606/1 |
| 5,746,764 | 5/1998 | Green et al. | 606/194 |
| 5,749,921 | 5/1998 | Lenker et al. | 623/1 |
| 5,752,941 | 5/1998 | Romano' et al. | 604/265 |
| 5,800,517 | 9/1998 | Anderson et al. | 623/1 |
| 5,810,873 | 9/1998 | Morales | 606/198 |
| 5,843,092 | 12/1998 | Heller et al. | 606/108 |
| 5,893,852 | 4/1999 | Morales | 606/108 |
| 5,925,061 | 7/1999 | Ogi et al. | 606/198 |
| 6,018,857 | 2/2000 | Duffy et al. | 29/407.01 |
| 6,068,635 | 5/2000 | Gianotti | 606/108 |

FOREIGN PATENT DOCUMENTS

| | | | |
|---|---|---|---|
| 295 06 654 U | 7/1995 | Germany | A61M 29/00 |
| 195 32 288 A1 | 3/1997 | Germany | A61M 29/00 |
| WO 98/19633 | 5/1998 | WIPO . | |

*Primary Examiner*—Paul J. Hirsch
*Assistant Examiner*—Michael B. Priddy
*Attorney, Agent, or Firm*—Todd P. Messal

[57] ABSTRACT

The present invention describes a device for delivering a stent to a bodily stricture. The delivery device advantageously includes a funnel shaped distal end configured to facilitate compressing the stent onto the delivery device. The funnel may further include a tear away strip suitable for separating the funnel from the delivery device.

10 Claims, 5 Drawing Sheets

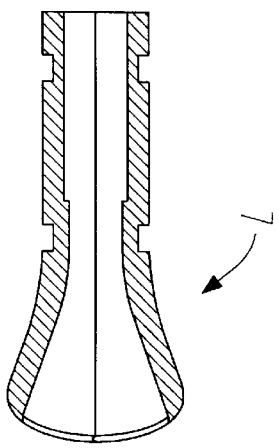
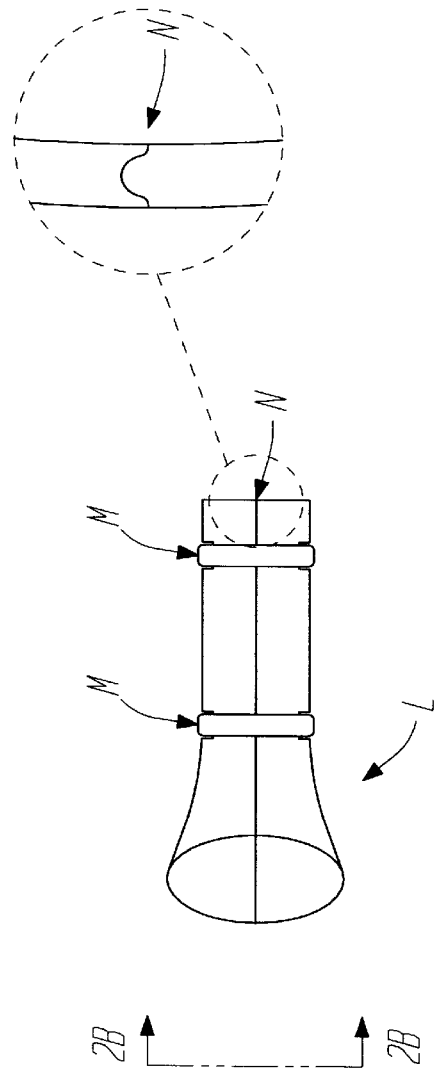
FIGURE 2B
FIGURE 2A

STENT LOADING TOOL

This application claims priority to U.S. Provisional Patent Application Ser. No. 60/087,919, filed Jun. 4, 1998.

FIELD OF THE INVENTION

The present invention generally relates to medical devices. More specifically, the present invention relates to an assembly comprising an implantable prosthesis, a system for delivering the prosthesis within the body, and a loading device which loads the prosthesis onto the delivery system. Those skilled in the art will recognize the benefits of applying the present invention to similar fields not discussed herein.

SUMMARY OF THE INVENTION

The present invention may be described as a stent loading tool having a peel away means which facilitates loading of a stent onto a stent delivery device. The present invention may also be described as a method of delivering the prosthesis. Other aspects and advantages of the present invention can be fully appreciated with a thorough review of the entire specification and drawings. Those skilled in the art will appreciate other advantages not fully described herein. Furthermore, while the disclosure focuses on bioabsorbable stents, those skilled in the art will recognize that the invention may be incorporated into other devices and methods of use without departing from the spirit of the invention.

BRIEF DESCRIPTION OF THE DRAWINGS

FIG. 2 depicts an alternative embodiment of the invention.

DETAILED DESCRIPTION OF THE INVENTION

Figure 1D:
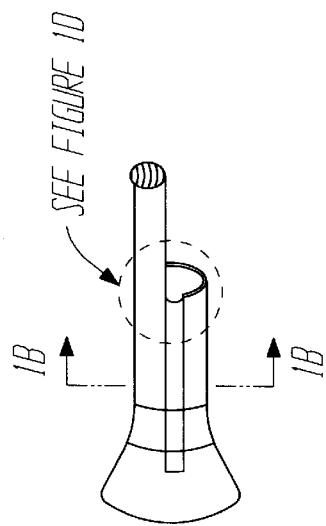
FIG. 1 depicts an embodiment of the invention.
Figure 1C:
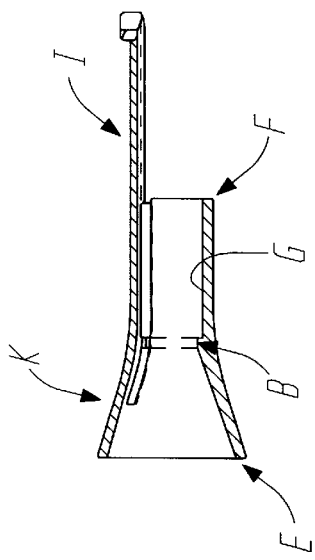
Figure 1A:
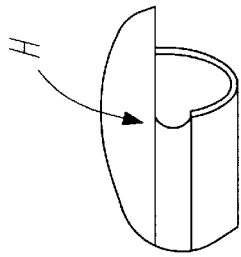
Figure 1B:
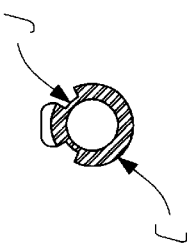

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

The present invention relates to an assembly comprising three separate components: an implantable bioabsorbable stent, a delivery system, and a stent loading funnel. The implantable stent is preferably loaded onto the delivery system at the time of implantation.

The Stent

The implantable stent may be made of bioabsorbable polylactide filaments braided in a tubular mesh configuration. This design configuration results in a self-expanding stent with dynamic radial force that is both flexible and compliant. The implanted stent will naturally be absorbed in vivo. The stent may retain up to 80% of its original radial strength for up to eight months post implantation. Stent absorption may be complete from 1.5 to 2.0 years post implantation. Absorption rates, however, will vary by individual.

The implantable stent is preferably individually packaged and contained in the shelf carton with the delivery system. The bioabsorbable implantable stent may generally have a tubular, radially compressible and self-expandable braided and annealed structure including a first set of between 5 and 18 filaments, each of which extends in a helix configuration along a center line of the stent and having a first common direction of winding. A second set of filaments of the same number as the first set, each extend in a helix configuration along a center line of the stent and having a second common direction of winding. The second set of filaments cross the first set of filaments at an axially directed angle of between about 120 and about 150 degrees when in a first free radially expanded state after being annealed, but before being loaded on a delivery device so as to form a plurality of interstices between filaments.

The term "free state" is used when no externally applied forces are acting on the device, for example, when the device is resting on a table. Each filament includes PLLA, PDLA, PGA, or combinations thereof and have a substantially solid and substantially uniform cross-section, a tensile strength of from about 40 ksi to about 120 ksi, a tensile modulus of from about 400,000 psi to about 2,000,000 psi, and an average diameter of from about 0.15 mm to about 0.6 mm. The first set of filaments and second set of filaments act upon one another to create an outwardly directed radial force sufficient to implant the stent in a body vessel upon deployment from a delivery device. The stent may have a second free radially expanded state after being loaded and then released from a deployment device and the first and second sets of filaments cross at an axially directed angle of between about 80 and about 145 degrees when in the second free radially expanded state.

The stent may have an implanted state after being loaded, released from a deployment device into a body vessel, and then implanted in the body vessel, with the first and second sets of filaments crossing at an axially directed angle of between about 95 and 105 degrees when the stent is in the implanted state. The stent may be radially constrained to half of its free diameter and the radial force, RF, exerted by the device, in grams, as a function of annealed diameter, D, in mm, is about $RF = -15D + 491 \pm 20$.

The stent may be annealed at a temperature of from about 60° C. to about 180° C. for a period of time of from about 5 minutes to about 120 minutes. The stent may be annealed at a temperature of from about 130° C. to about 150° C. for a period of time of from about 10 minutes to about 20 minutes. The braid may be annealed to yield a crossing angle of from about 130 degrees to about 150 degrees. The stent may be further disposed in a stent delivery device and the filaments have a crossing angle of from about 30 degrees to about 120 degrees. The stent may be deployed from a delivery system into a body lumen and the filaments have a crossing angle of from about 70 degrees to about 130 degrees. The stent may provide structural integrity to a body lumen for less than about three years.

The stent may further include polydioxanone, polycaprolactone, polygluconate, polylactic acid-polyethylene oxide copolymers, modified cellulose, collagen, poly(hydroxybutyrate), polyanhydride, polyphosphoester, poly(amino acids) and combinations thereof. The filaments may be mono-filament or multi-filament. The stent may substantially degrade in vivo in from about 1 year to about 2 years. "Substantially degrade" means that the stent has lost at least 50% of its structural strength. It is preferable that the stent lose about 100% of its structural strength. The filaments may include polyglycolide and the stent may substantially degrade in vivo in a time of from about 3 months to about 1 year. The filaments may further include polygluconate, polydioxanone, or combinations thereof and the stent may substantially degrade in vivo in from about 1 week to about 3 months.

The filaments may further be substantially homogeneous in cross section and length. The filaments may have a tensile modulus of from about 400,000 psi to about 1,200,000 psi. The stent may include a plurality of the filaments helically wound and interwoven in a braided configuration to form a tube. The stent may also be constructed of metallic elements and have a configuration of a braided tubular mesh of individual strands of metal wire, a zig-zag metal wire form, or a slotted metal tube. The stent may also have a coating or covering attached to the structural elements. In addition to stents, other endoluminal prostheses may be used including filters and occlusion devices.

The Delivery System

The delivery system is comprised of coaxial tubes. The exterior tube serves to constrain the stent until retracted during deployment. Radiopaque marker bands situated adjacent to the leading and trailing ends of the stent facilitate imaging during deployment. The interior tube of this coaxial system contains a central lumen that accommodates a guide wire, preferably an 0.035" guide wire. Examples of suitable delivery systems which do not contain loading tools are described in U.S. Pat. Nos. 5,026,377 and 5,484,444, which are incorporated herein by reference. An example of a loading system is describe in co-pending a U.S. patent application Ser. No. 08/947,450 which is also incorporated by reference.

The Stent Loading Funnel

A removable funnel-shaped stent loading tool may be mounted on the distal end of the delivery system. The stent loading funnel facilitates mounting of the implantable stent prior to implantation by providing a uniform diameter decrease of the stent as the exterior tube is advanced over the stent.

Referring now to FIG. 1, the stent loading funnel may utilize fluorinated heat shrunk heatshrink to create a funnel to fit over the distal end of the exterior tube of the stent delivery system. An alternative version may be injection molded, such as with a linear low-density polyethylene or polypropylene. The primary features are the funnel (E) and the fitted end (F).

The design is such that the stent is constrained to a reduced diameter by advancing the exterior tube over the stent. Features that help to accomplish this efficiently are the waist (B) to which the stent is constrained, and the ledge (G) against which the exterior tube rests. This ledge is dimensioned such that the distal end of the exterior tube is covered by the ledge, i.e. the smallest inside diameter of the funnel ledge is less than or equal to the inside diameter of the exterior tube. The ledge allows the stent to slide inside the exterior tube without the stent wires or filaments catching on the exterior tube and bending or possibly breaking as the exterior tube is advanced.

As can been seen in FIGS. 3–9, loading funnel 35 is mounted on the distal end of exterior tube 15. Preferably, funnel 35 is held in place by friction or a snug fit. Alternatively, funnel 35 may be made of a heat shrinkable polymer which is heat shrunk unto exterior tube 15. Because the inside diameter of funnel 35 is smaller than the external diameter of tip 70, funnel 15 is preferably mounted on exterior tube 15 before tip 70 is attached to inner member 40.

The peel-away loading funnel shown in FIG. 1 may have several additional features to provide the following benefits; better fit over the catheter, better fit at the catheter ID, one time use, ease of manufacturability, easier removal from the delivery system, reduced risk of distal tip bond damage upon removal of the funnel, and it may be used with a correctly sized distal tip.

A feature that provides these benefits is the peel-away tear strip (I), that is to be pulled to remove the loading funnel from the delivery system after the stent has been loaded. The strip tears along a thin walled section (J). The tear originates at tear starts (H) located at the proximal end of the thin walled channels. The tear strip proceeds distally, until the funnel width at the end of the tear strip (K) is sufficiently wide to accommodate the delivery system distal tip. The loading funnel may then be removed in one piece. Alternatively, the tear could originate at the distal end of the funnel so that the funnel can be advanced over the tip as the exterior tube is advanced distally.

An alternative embodiment of the stent loading funnel is depicted in FIG. 2 where two identical halves (L) are held together by binders (M). The halves (L) mate to prevent slipping (N). The inner profile of the loading tool may be identical to the peel-away funnel, providing the same degree of assistance in loading the stent onto the delivery system.

Principal of Operation of Preferred Embodiment

The bioabsorbable endoprosthesis may be used to treat a variety of bodily strictures including vascular, esophageal, urinary, colo-rectal, and pallative treatment of bile duct strictures caused by malignant neoplasms.

The delivery system may be prepared by first obtaining materials required to perform the implantation procedure. Those materials may include an endoprosthesis, a guide wire, a syringe filled with sterile saline, an endoscopy station including an endoscope with preferably a 4.2 mm working channel and any other conventional endoscopy devices and supplies.

Figure 3:
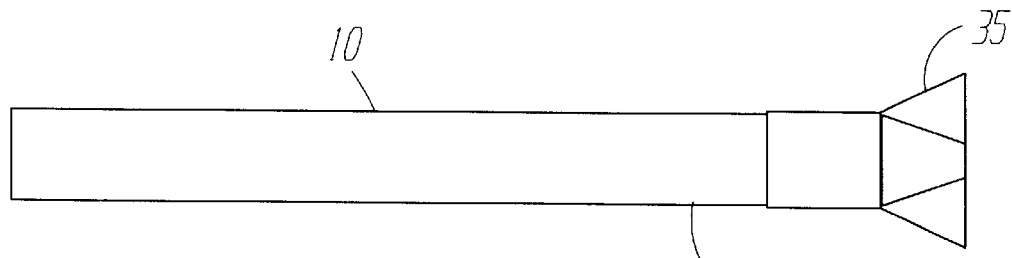
FIGS. 3–10 depict use of an embodiment of the invention.

The endoprosthesis may be loaded onto the delivery system in the following manner. As depicted in FIG. 3, the delivery system 10 arrives in the closed position. The exterior tube 15 may then be retracted until the distal end of the stent loading funnel 35 is aligned with the trailing marker band 20.

Figure 4:
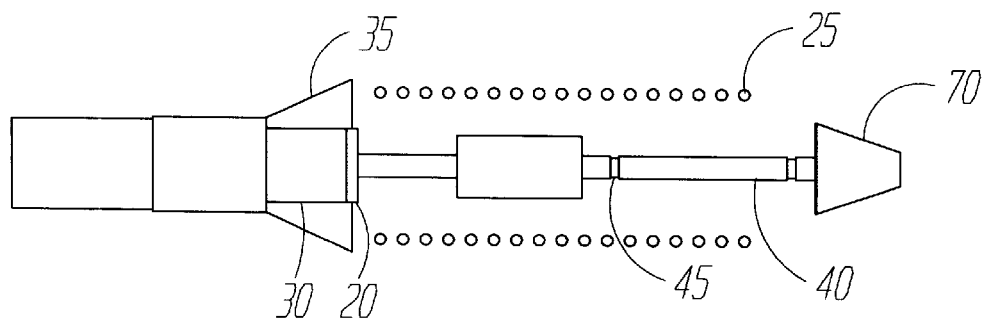
Figure 5:
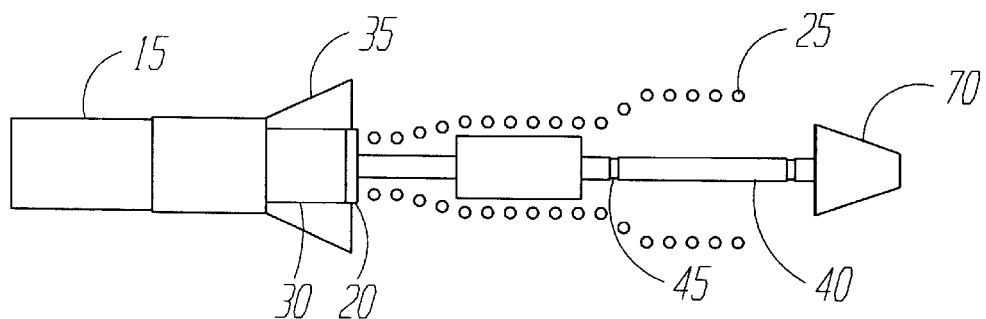

In FIG. 4 a stent 25 may be placed over the exposed inner member 40. As shown in FIG. 5, the stent 25 may then be manually constrained by compressing the stent 25 so that it will fit inside the stent loading funnel 35 and abut the stent against the inner member jacket 30 at the trailing marker band 20.

Figure 6:
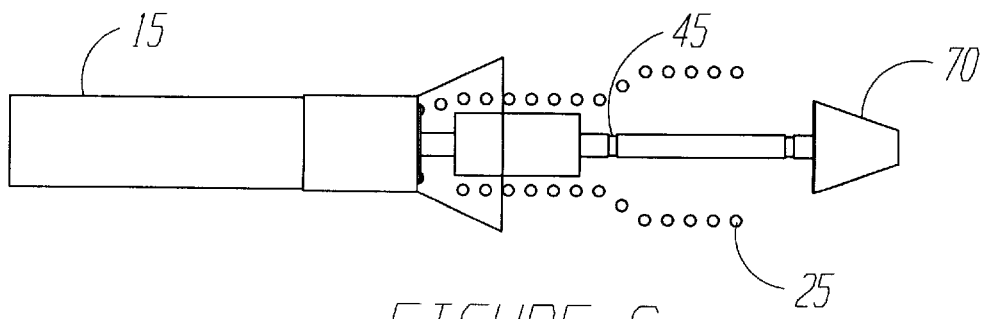
Figure 7:
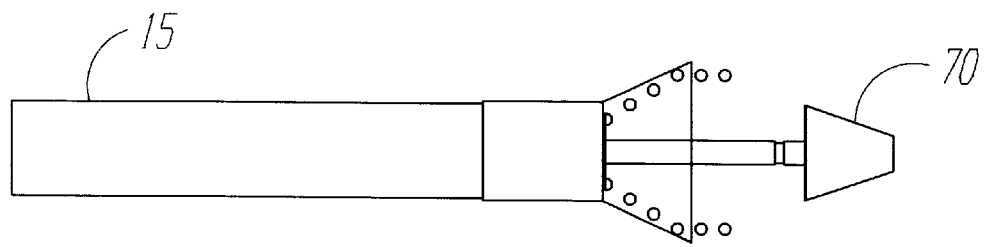
Figure 8:
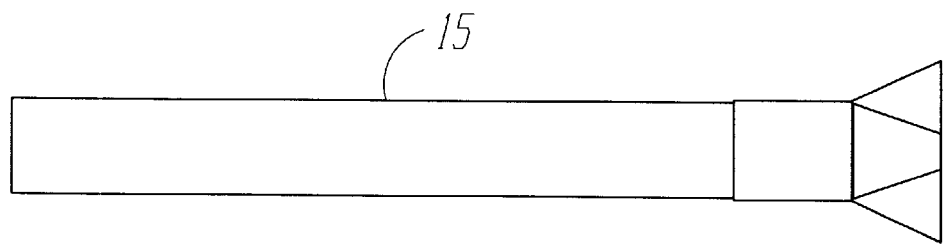
Figure 9:
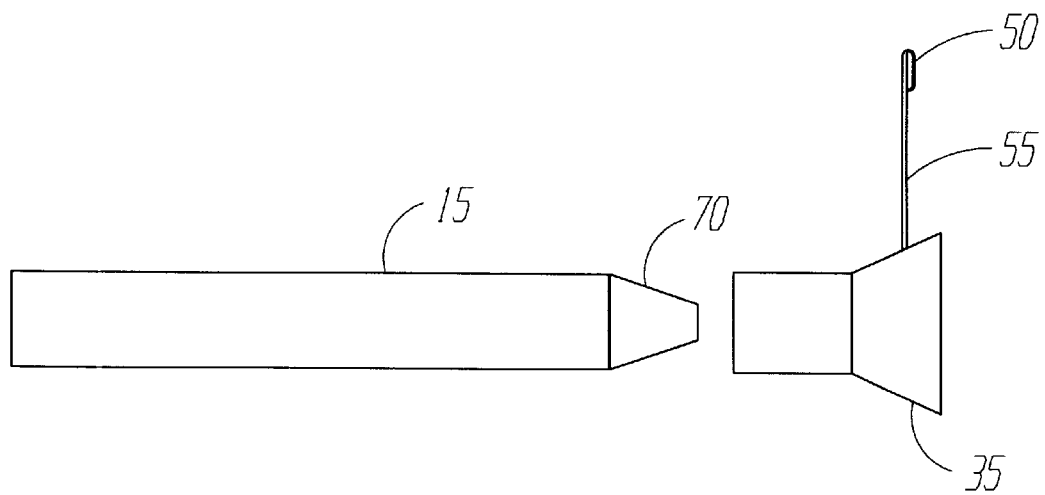

Next the exterior tube 15 may be advanced over the constrained stent 25, depicted in FIG. 6. FIG. 7 shows that the exterior tube 15 may be advanced beyond the limit marker 45 while the stent is constrained by advancing the exterior tube 15. The exterior tube 15 may be further advanced until, in FIG. 8, the exterior tube 15 is positioned such that the stent 25 is fully constrained. Finally, in FIG. 9, the loading funnel 35 may be removed by grasping the tab 50 and pulling the peel strip 55.

Figure 10:
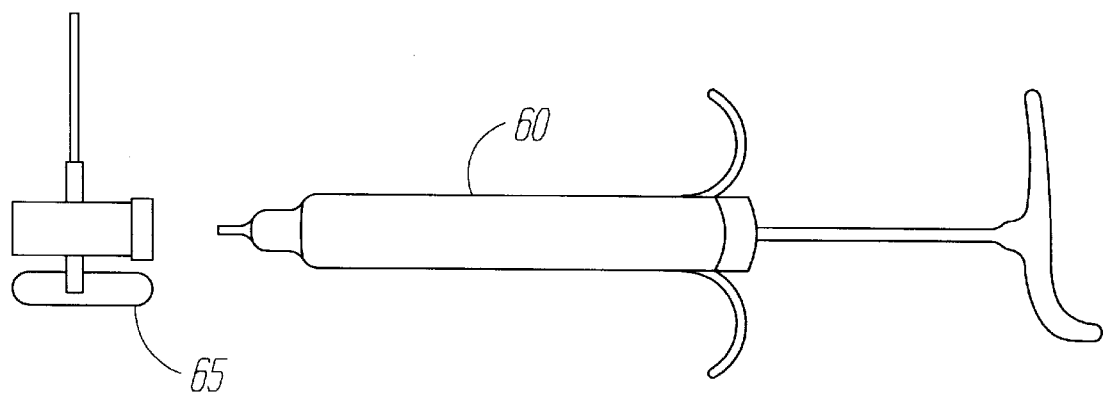

In FIG. 10 a syringe 60 filled with saline may be affixed to a stopcock 65. Saline may then be injected until flow from the tip of the delivery system is visually confirmed. Once flow from the tip is confirmed, the stopcock may be closed and the syringe may be removed.

The implantable stent is mounted onto the delivery system preferably shortly prior to the implantation procedure. The delivery system with mounted stent is advanced over a guide wire and into the working channel of an endoscope until radiopaque markers on the delivery system are aligned with the stricture to be treated. Deployment is initiated by retracting the outer tube of the delivery system while holding the inner tube stationary. The implantable stent self-expands from the delivery system.

The deployment process may be reversed if stent repositioning is desired. The stent may be reconstrained by the exterior tube if the stent deployment threshold is not exceeded. Once reconstrained, the stent may be repositioned either distal or proximal and the deployment process restarted. Full retraction of the outer tube completely liberates the stent from the delivery system. Post dilation of the stent with a balloon may be used to complete the implantation procedure.

While the specification describes the preferred constructions, materials, dimensions, methods of manufacture and methods of practice, those skilled in the art will appreciate the scope and spirit of the invention with reference to the appended claims.

We claim:

1. A stent delivery device comprising:

an elongate member having a distal portion;

a tube slideably mounted about the distal portion of the member, the tube having a distal end; and a stent loading funnel mounted on the distal end of the tube and comprising a peel away means for removing the stent loading funnel after the stent has been mounted on the delivery device.

2. The peel away means of claim 1 further comprising a tear away strip.

3. The tear away strip of claim 2 wherein the tear away strip tears in a direction parallel to a longitudinal axis of the delivery device.

4. An assembly for delivering an endoprosthesis to a bodily stricture comprising:

an exterior tube; and an interior member slideably mounted within the exterior tube, the interior member configured to constrain the endoprosthesis relative to the exterior tube; and a funnel surrounding the interior member adjacent a distal end of the exterior tube and comprising a tear away strip, the funnel assisting the endoprosthesis in transitioning from an uncompressed state to a compressed state as the exterior tube is slid over the interior tube.

5. The funnel of claim 4 further comprising:

a distal portion having an inner diameter which decreases proximally;

a body portion located proximally to the distal portion and having a generally constant inner diameter; and an annular ledge defined by a reduced inner diameter portion of the funnel located at the transition between the distal portion and the body portion, the ledge configured to seat the funnel about the distal end of the exterior tube.

6. The interior member of claim 4 further comprising an at least one marker band.

7. The assembly of claim 4 further comprising a jacket member fixedly attached to the interior member, the jacket configured to prevent movement of the endoprosthesis relative to the exterior or interior tubes.

8. A method of mounting an endoprosthesis on a delivery device comprising:

providing a stent, a loading tool having an interior tube slideably mounted within an exterior tube and a loading funnel attached to a distal end of the exterior tube, the loading funnel having a tear away strip suitable for detaching the funnel from the exterior tube;

loading an uncompressed endoprosthesis about the delivery device;

advancing the exterior tube over the stent and thereby causing the endoprosthesis to be compressed about the delivery device; and removing the loading funnel by tearing away the tear away strip.

9. The method of mounting an endoprosthesis on a delivery device of claim 8 further comprising abutting the endoprosthesis against a marker band, the marker band affixed to the loading tool.

10. The method of mounting an endoprosthesis on a delivery device of claim 8 further comprising manually compressing the endoprosthesis prior to the step of advancing the exterior tube over the stent.

* * * * *